United States Patent [19]

Serola

[11] Patent Number: 5,201,761
[45] Date of Patent: Apr. 13, 1993

[54] DEVICE AND METHOD FOR REDUCING LUMBAR LORDOSIS WHILE SUPINE AND SUPPORTING THE LUMBAR CURVE WHEN SEATED

[76] Inventor: Richard J. Serola, 6600 Kalanianaole Hwy., Suite 208, Honolulu, Hi. 96825

[21] Appl. No.: 790,518

[22] Filed: Nov. 12, 1991

[51] Int. Cl.⁵ .......................... A61G 15/00; A61F 5/00
[52] U.S. Cl. ..................................... 606/240; 128/845; 5/653
[58] Field of Search ...................... 297/284 D, 284 E; 5/652–654, 630, 644, 636; 606/237, 240, 241; 602/5, 6, 13, 19, 32, 35; 128/845, 846, 870

[56] References Cited

U.S. PATENT DOCUMENTS

| | | | |
|---|---|---|---|
| 2,769,185 | 11/1956 | Biederman | 5/653 |
| 3,017,221 | 1/1962 | Emery | 5/644 X |
| 3,644,949 | 2/1972 | Diamond | 5/630 |
| 4,483,329 | 11/1984 | Shamos | |
| 4,516,568 | 5/1985 | Baxter et al. | 297/284 E X |
| 4,835,801 | 6/1989 | Walpin et al. | 5/652 |

*Primary Examiner*—Richard J. Apley
*Assistant Examiner*—Linda C. M. Dvorak
*Attorney, Agent, or Firm*—Warren F. B. Lindsley

[57] ABSTRACT

A dual purpose pillow for reversing the lordotic curve of a patient by acting on the base of the spine and comprises two wedges that act complimentary to each other. A larger wedge of the pillow is higher at the foot end and lower at the head end of the patient and acts to place the pelvis into posterior tilt. The sacrum is carried along with the pelvis into posterior pelvic tilt. The smaller wedge of the pillow is also higher at the foot end and lower at the head end of the patient and further increases the posterior tilt of the sacrum, thus acting to reduce the disc wedge angle above the sacrum. This pillow may be used to support the lumbar spine and musculature while the patient is sitting.

5 Claims, 2 Drawing Sheets

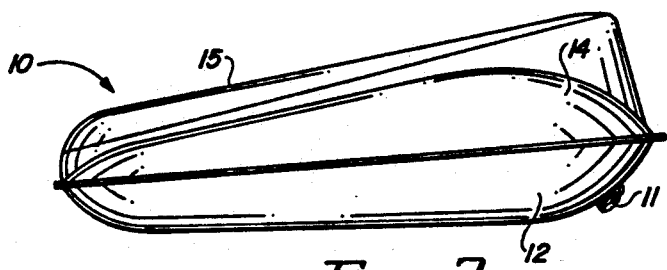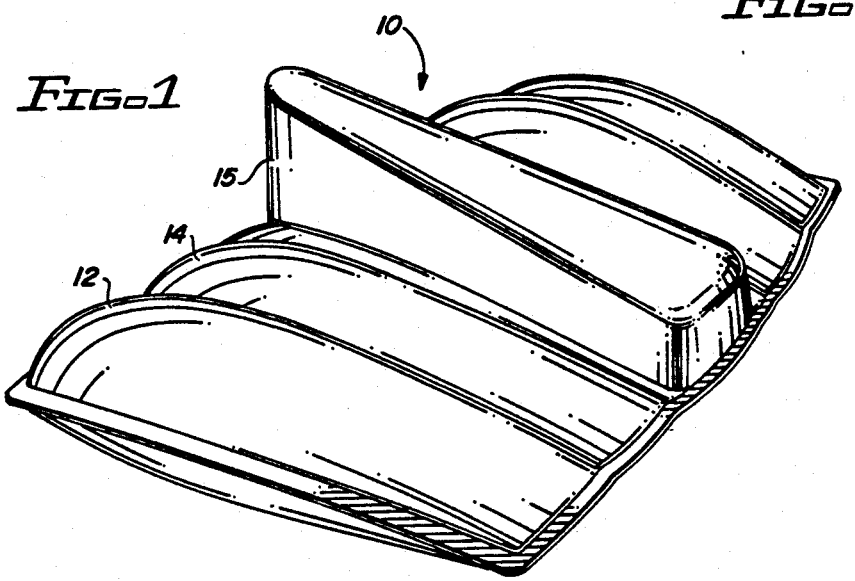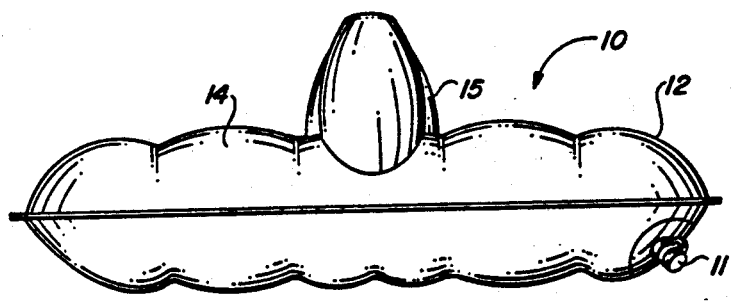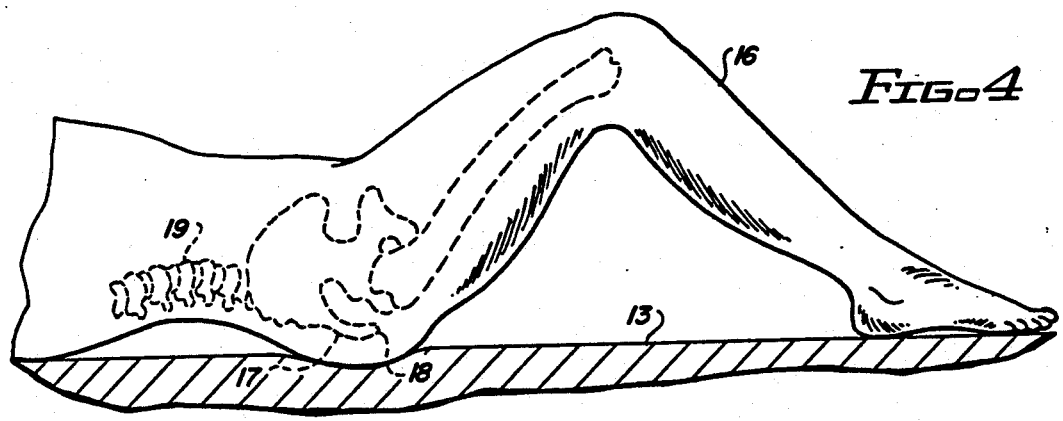

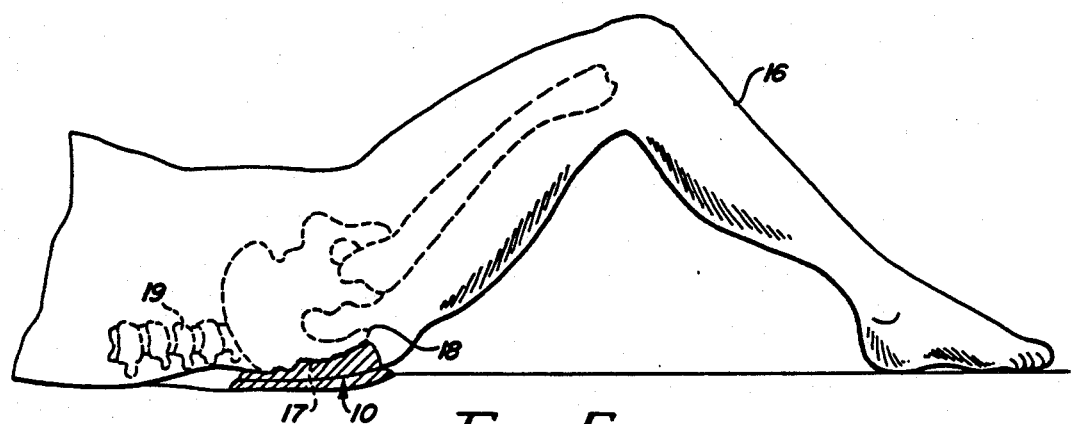
FIG. 5
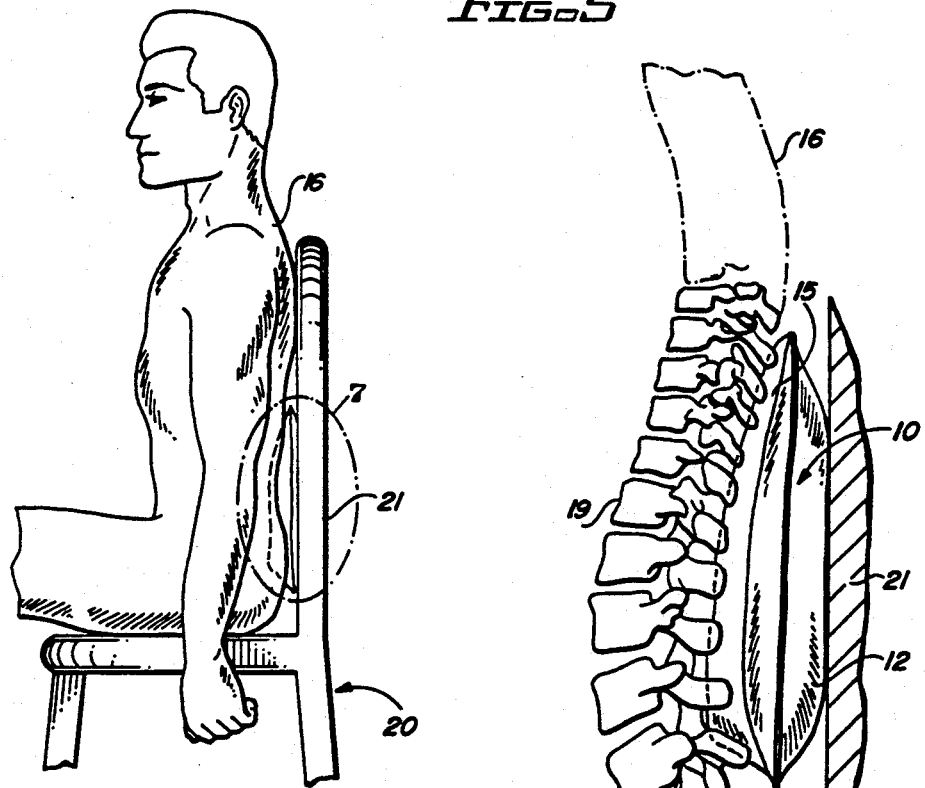
FIG. 6
FIG. 7

DEVICE AND METHOD FOR REDUCING LUMBAR LORDOSIS WHILE SUPINE AND SUPPORTING THE LUMBAR CURVE WHEN SEATED

BACKGROUND OF THE INVENTION

This invention relates to a device and method for reducing lumbar lordosis while supine and supporting the lumbar curve when seated.

Backaches in the lumbar region of the spine are common in today's society and are usually attributed to bad posture or excess weight in the stomach area.

The normal curvature of the lumbar spine is lordotic. By lordotic it is meant that, when observing the human body from the side, the lumbar curve has a convexity toward the anterior of the body. Increased lumbar lordosis, i. e., hyperlordosis, may be described as a lordotic curve that is increased beyond normal physiological homeostasis and results in an imbalance of the structure. Joint irritation, ligamentous stress, muscle spasm, and pain may all be associated with hyperlordosis.

Low backaches can be relieved by reducing the degree of lumbar lordosis. This can be done by manipulating the sacral area to restore the lumbar region of the spine and the sacrum to their proper attitudes and positions. Normally, such manipulation is done by trained therapists or practitioners.

The purpose of the invention is to relieve hyperlordosis and/or support the lumbar curve while sitting.

The pillow disclosed and claimed herein reverses the lordotic curve by acting on the base of the spine and provides two wedges that act complimentary to each other. The larger wedge of the pillow is higher at the foot end and lower at the head end of the patient and acts to place the pelvis into posterior tilt. The sacrum is carried along with the pelvis into posterior pelvic tilt. The smaller wedge of the pillow is also higher at the foot end and lower at the head end and further increases the posterior tilt of the sacrum, thus acting to reduce the disc wedge angle above the sacrum. The disc wedge angles throughout the lumbar spine are similarly affected. The lordotic curve is reduced to a point past normal lordosis so that, when the device is removed, some correction is maintained.

The lumbar spine and musculature that exhibits weakness and/or pain may find relief when a support is placed between the lumbar curve and the seat. The more the support conforms to the shape of the lumbar spine and musculature, the greater will be the relief obtained because pressure will be distributed more evenly. Because the vertebrae of the spine form the basis of the support structure of the back, a device that supplies support directly to the vertebrae, as well as directly to the musculature of the back, will provide greater support than one that supplies support directly to the musculature only, and indirectly to the vertebrae.

Lumbar support pillows currently available are designed to curve as close as possible to the lumbar curve but give direct support primarily to the musculature.

The difficulty in supporting the lumbar vertebrae and the musculature simultaneously and equally arises from the fact that the vertebrae may be deeply anterior to the muscular portion of the lumbar area of the back, especially on well muscled individuals. The supporting device must be able to conform itself in such a manner that it will fill the longitudinal depression that is formed by the vertebrae in the center of the back. Inflatable lumbar supports exist that attempt to fill this need but they do not completely or adequately fill the longitudinal depression formed by the vertebrae of the patient.

DESCRIPTION OF THE PRIOR ART

U.S. Pat. No. 4,483,329 discloses a device for reducing lumbar lordosis that is shaped to fit the sacral area of a supine patient to provide support for the apex of the sacrum without providing support for the base of the patient's sacrum. The body weight of such a supine patient will bias the sacrum to reduce lumbar lordosis and thereby alleviate low backache.

SUMMARY OF THE INVENTION

In accordance with the invention claimed, a new and improved object is disclosed which effectively reduces lumbar lordosis in the supine position and supports the lumbar curve when in the seated position.

This object, i. e. pillow, simultaneously supports the lumbar musculature and the vertebrae of the patient and comprises two wedges. A smaller wedge is formed on top of the center of a larger wedge. The pillow is placed behind the lumbar curve with its narrow end toward the head of the patient and the smaller wedge facing the back of the patient. The larger wedge conforms to the shape of the lumbar musculature and supplies support to the musculature. The smaller wedge fits into the longitudinal depression of the back made by the vertebrae and gives additional support to the boney structure of the back.

It is, therefore, one object of this invention to provide a new and improved pillow shaped to provide support for the sacrum of a user when in a supine position and employing the body weight of the patient to reduce lumbar lordosis.

Another object of this invention is to provide an air inflatable pillow having a base surface for supporting the pelvis of a user when supine on a supporting surface and an upper wedge shaped surface for supporting the sacrum during use.

A still further object of this invention is to provide a new method of reducing lumbar lordosis in a patient.

A still further object of this invention is to provide a new pillow and method of use for supporting the lumbar spine and musculature while the user is sitting.

Further objects and advantages of this invention will become apparent as the following description proceeds, and the features of novelty which characterize the invention will be pointed out with particularity in the claims annexed to and forming a part of this specification.

BRIEF DESCRIPTION OF THE DRAWINGS

The present invention may be more readily described by reference to the accompanying drawings in which:

FIG. 1 is a perspective view of a pillow for reducing lumbar lordosis in a patient and embodying the invention;

FIG. 2 is a right side view of FIG. 1;

FIG. 3 is a back view of FIG. 1;

FIG. 4 is a fragmentary, schematic side elevational view of a patient with lumbar lordosis resting in a supine position on a surface;

FIG. 5 is a view similar to FIG. 4 with a pillow placed in its operative position to thereby reduce lumbar lordosis;

FIG. 6 is a side view of a patient in a seated position with the pillow supporting the lumbar spine and musculature; and FIG. 7 is an enlarged schematic side elevational view of the circled area 7 of FIG. 6 of a patient resting in a seated position on a chair with the pillow in position to support the lumbar spine and musculature.

DESCRIPTION OF THE PREFERRED EMBODIMENT

Referring more particularly to the drawings by characters of reference, FIGS. 1-3 disclose a wedge shaped device or pillow 10 which may be formed of a non pervious material and air inflatable through a suitable valve 11 or filled with a suitable soft resilient rubber or plastic foam or any other suitable resilient fiber, rubber or plastic material.

The pillow as shown in FIGS. 1-3 comprises a first wedge shaped base portion 12 which is positioned against a horizontal supporting surface 13, shown in FIG. 4, and extends upwardly and outwardly therefrom. The wedge shaped base portion 12 of the pillow is higher at one end and lower at the other end and is intended to support the patient's pelvis.

As noted from FIGS. 1-3 of the drawings, pillow 10 is provided with a second wedge shaped portion 15 which extends outward and longitudinally from the top surface 14 of the pillow at substantially its center with the high portion of the second wedge shaped portion formed at a common end of the pillow with the high portion of the first wedge shaped portion of the pillow. This second wedge shaped portion 15 is intended to place pressure in the cavity at the base of the back on the vertebrae of the spine.

FIG. 4 illustrates a patient 16 resting in a supine position on surface 13 and exhibiting a sufficient degree of lumbar lordosis to produce distressing low backache.

FIG. 5 shows a view similar to that shown in FIG. 4 wherein patient 16 is resting on pillow 10 in accordance with the teaching of this invention for reducing lumbar lordosis.

It will be noted when comparing FIGS. 4 and 5 of the drawings that the apex 18 of sacrum 17 exhibits substantially a different angle relative to resting surface 13 in FIG. 4 than it does in FIG. 5. This while exaggerated, demonstrates the manner in which pillow 10 has pivotally displaced sacrum 17 of patient 16 to move the base of the sacrum in the posterior direction while moving apex 18 of the sacrum in the anterior direction. This causes lumbar region 19 to straighten until it is virtually linear and parallel to the resting surface 13 as shown in FIG. 5.

It must be appreciated that the second wedge shaped portion 15 of the pillow rests essentially against the sacrum of the patient while the first wedge shaped portion of the pillow rests essentially against the pelvis. The function of the second wedge shaped portion of the pillow causes, more effectively than the prior art, the lumbar region to straighten out.

It should be noted that in FIG. 4 the lordosis condition has been exaggerated as has the reduction in lumbar lordosis in FIG. 5. This has been done to clearly demonstrate the problem and the manner in which pillow 10 can eliminate or alleviate the problem.

It has been found by experiments as set forth in U.S. Pat. No. 4,483,329 which is incorporated herein by reference, that one-degree of reduction in the lumbosacral angle generally reduces lumbar lordosis sufficiently to alleviate low backache in an average patient.

FIGS. 1-3 and 5 illustrate that pillow 10 is shaped to fit the sacral area of a supine patient between the rear pelvic area of patient 16 and a surface 13 on which the patient is resting in a supine condition. The pillow forms a first wedge shaped portion 12 engaging essentially the pelvis and buttocks of the patient with a second wedge shaped portion 15 fitting the sacrum between the buttocks.

FIGS. 6 and 7 illustrate the use of pillow 10 in a seated position on a chair 20 with the pillow placed between the lower back of the patient and the back 21 of chair 20. As noted the wider position of the first and second wedges are at the base of the spine of the patient.

Pillow 10 when expanded may comprise a first wedge shaped portion having a rectangular base of approximately 14 inches in length and a width of approximately 12 inches with the second wedge shaped portion extending longitudinal of the base along its axis and being narrower in width than the first wedge shaped portion. The second wedge shaped portion may extend approximately 2¼ inches above the higher end of the wedge forming the base of the pillow and having a width of approximately 2 inches at the lower end and ⅞ inch at the higher end of the pillow.

The top of the first wedge shaped portion is creased longitundinally of the pillow and the top of the second wedge shaped portion may be flat or conical, as desired.

The prior art as represented by U.S. Pat. No. 4,483,329 heretofore referred to provides "support for the apex of the patient's sacrum without providing support for the base of the patient's sacrum.

Because the claimed pillow conforms to the user's sacrum, it effectively cradles the sacrum. This cradling effect allows the pillow to grip the sacral base area and traction the sacrum footward as the user's weight is displaced headward by the effect of the pillow's wedge shape.

At the same time, the pillow displaces the sacral apex anteriorly. The net effect is a rotation of the sacrum about an axis perpendicular to its length and at its approximate center of gravity, while causing a footward tractioning effect on the sacrum at the same time. This is different than the prior art in that the prior art does not contact the base area of the sacrum.

Also, the claimed invention provides support for the base of the sacrum whereas the prior art does not. In addition, to the traction effect above described, contact at the sacral base helps prevent excess jamming of the sacroiliac articulations. Although much more pressure is placed at the apex of the sacrum that effectively rotates and pushes the sacrum into the two iliac bones by the claimed pillow, a small amount of cushion is placed at the sacral base to prevent excess jamming of the sacroiliac articulations.

Although but one embodiment of the invention has been shown and described, it will be apparent to those skilled in the art that various changes and modifications may be made therein without departing from the spirit of the invention or from the scope of the appended claims.

What is claimed is:

1. A dual purpose pillow for support of the lumbar spine while the user is sitting and reduction of lumbar lordosis with simultaneous traction of the lumbosacral spine while the user is supine comprising:

a base member for engaging a flat supporting surface, said base member forming a first wedge shaped portion having a continuous slope along substantially its full length with the high end of said first wedge shaped portion being at one end of the pillow and the low end of said first wedge shaped portion being at the other end of said pillow, and a second wedge shaped portion extending outwardly of said first wedge shaped portion and having a continuous slope with the high end of said second wedge shaped portion being at the high end of said first wedge shaped portion and the low end of said second wedge shaped portion being at the other end of said first wedge shaped portion, said second wedge shaped portion being narrower in width than said first wedge shaped portion and extending substantially along the full length of the longitudinal axis of said first wedge shaped portion, said first wedge shaped portion of said pillow resting essentially against the user's pelvis with said second wedge shaped portion being positioned to cradle the user's sacrum to displace its apex anteriorly when the user is in a supine position, whereby the pillow pulls the sacrum into its articulation with the iliac bones of the pelvis thereby reducing stress on the sacroiliac ligaments of the user when the user is in a supine position.

2. The support pillow set forth in claim 1 wherein:
the width of said second wedge shaped portion is narrow enough to fit longitudinally of the user in the cavity of his or her back when in the seated position.

3. The support pillow set forth in claim 1 wherein:
the width of said second wedge shaped portion is substantially two inches at its low end and ¾ of an inch at its high end.

4. The support pillow set forth in claim 1 wherein:
the pillow is formed of a non-pervious material that is inflatable through a valve in said pillow.

5. The support pillow set forth in claim 1 wherein:
said second wedge shaped portion is positionable to conform to and support the user's lumbar curve when the user is in a seated position with the pillow between the user and the back of a chair.

* * * * *